(12) United States Patent
Zuckerman et al.

(10) Patent No.: US 7,002,003 B1
(45) Date of Patent: Feb. 21, 2006

(54) METHOD FOR THE INHIBITION OF FUNCTION OF STAT TRANSCRIPTION FACTORS

(75) Inventors: Kenneth S. Zuckerman, Tampa, FL (US); Richard Y. Liu, Lutz, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/744,875

(22) PCT Filed: Jul. 30, 1999

(86) PCT No.: PCT/US99/17366

§ 371 (c)(1),
(2), (4) Date: Apr. 30, 2001

(87) PCT Pub. No.: WO00/06696

PCT Pub. Date: Feb. 10, 2000

Related U.S. Application Data

(60) Provisional application No. 60/094,695, filed on Jul. 30, 1998.

(51) Int. Cl.
  C07H 21/04 (2006.01)
  A61K 48/00 (2006.01)
  C12N 15/00 (2006.01)
(52) U.S. Cl. .................. 536/24.1; 536/24.5; 536/23.1; 514/44
(58) Field of Classification Search ............ 435/6, 435/91.1, 325, 366, 375; 536/23.1, 24.31, 536/24.33, 24.5; 514/44
See application file for complete search history.

(56) References Cited

U.S. PATENT DOCUMENTS

| | | | |
|---|---|---|---|
| 4,439,196 A | 3/1984 | Higuchi | |
| 4,447,224 A | 5/1984 | DeCant, Jr. | |
| 4,447,233 A | 5/1984 | Mayfield | |
| 4,475,196 A | 10/1984 | La Zor | |
| 4,486,194 A | 12/1984 | Ferrara | |
| 4,487,603 A | 12/1984 | Harris | |
| 4,666,828 A | 5/1987 | Gusella | |
| 4,683,202 A | 7/1987 | Mullis | |
| 4,801,531 A | 1/1989 | Frossard | |
| 4,925,678 A | 5/1990 | Ranney | |
| 4,959,217 A | 9/1990 | Sanders | |
| 5,034,506 A | 7/1991 | Summerton et al. | |
| 5,167,616 A | 12/1992 | Haak | |
| 5,169,383 A | 12/1992 | Gyory | |
| 5,192,659 A | 3/1993 | Simons | |
| 5,225,182 A | 7/1993 | Sharma | |
| 5,272,057 A | 12/1993 | Smulson | |
| 5,712,094 A * | 1/1998 | Seidel et al. | |

6,448,011 B1 * 9/2002 Bard et al.

FOREIGN PATENT DOCUMENTS

WO    WO 95/28482    * 10/1995

OTHER PUBLICATIONS

Dzau, Victor, Circulation Research, vol. 20, pp. 1234-1236, 2002.*
Jen et al., Stem Cells, vol. 18, pp. 307-319, 2000.*
Green et al. J. of Am. Coll. Surg. vol. 191, No. 1, Jul. 2000.*
Agrawal et al. Molecular Medicine Today, vol. 6, pp. 72-81, Feb. 2000.*
Ma et al., Biotechnology Annula Review, vol. 5, pp. 155-196, 2000.*
Branch, TIBS 23, pp. 45-50, Feb. 1998.*
Flanagan et al., Nature Biotechnology, vol. 17, No. 1, pp. 48-52, Jan. 1999.*
Bennett et al. "Pharmacology of Antisense Therapeutic Agents", Chapter 2, from Methods in Molecular Medicine: Antisense Therapeutics, Ed. S. Agrawal, Humana Press Inc., Totowa, NJ, ISBN: 0_89603-305-8, 1996.*
Liu et al. Experimental Hematology, vol. 25, No. 8, p. 764, 1997.*
Boccaccio et al., Nature, vol. 391, Jan. 15, 1998, p. 285-288.*
Pearse et al., PNAS vol. 90:4313-4318, May 1993.*
Wegenka et al., Molecular and Cellular Biology vol. 13(1): 276-288, 1993.*
Agarwal et al (1996). Antisense oligonucleotides: towards clinical trials, TIBTECH, 14:376.
Ausubel et al. Current Protocols in Molecular Biology, INDEX 1990, Suppl. 13.
Eckstein (1985). Nucleoside Phosphorothioates. Ann. Rev. Biochem. 54:367-402.
Iyer et al. (1990) J. Org. Chem. 55:4693-4699.
Mishell and Shiigi (eds), Selected Methods in Cellular Immunology, pp. 23&24.
Sambrook et al. Molecular Cloning: A Laboratory Manual, Cold Springs Harbor Laboratory, New York (1989, 1992), pp. 16.30-16.56.

(Continued)

Primary Examiner—Sean McGarry
(74) Attorney, Agent, or Firm—Saliwanchik, Lloyd & Saliwanchik

(57) ABSTRACT

There is provided a method of modulating the function of transcription factor by administering an effective amount of an oligonucleotide containing optimal nucleotide binding sites for the transcription factor. A therapeutic agent having an effective amount of an oligonucleotide for modulating function of transcription factors and a pharmaceutically acceptable carrier is also provided. Also provided is a treatment of patients having illnesses in which the activation of transcription factors play a role by administering to a patient an effective amount of an oligonucleotide which competitively binds the related transcription factor.

8 Claims, 6 Drawing Sheets

OTHER PUBLICATIONS

Shaw et al (1991). Modified deoxyoligonucleotides stable to exonuclease degradation in serum. Nucleic Acids Res. 19:747-750.

Spitzer and Eckstein (1988). Inhibition of deoxynucleases by phosphorothioate groups in oligodeoxyribonucleotides. Nucleic Acids Res. 18:11691-11704.

Stites et al (eds), Basic and Clinical Immunology (8th Edition).

Taylor (1980) J. Histochem, Cytochem 28:1021.

Testoni et al (1996), Blood 87:3822.

Dusanter-Fourt et al. "Identification of JAK protein tyrosine kinases as signaling molecules for prolactin. Functional analysis of prolactin receptor and prolactin- erythropoietin receptor chimera expressed in lymphoid cells," *The EMBO Journal,* 1994, vol. 13, No. 11, pp. 2583-2591.

Gewirtz et al. "Nucleic Acid Therapeutics: State of the Art and Future Prospects," *Blood,* 1998, vol. 92, No. 3, pp. 712-736.

Gorodetsky et al. "Isolation and characterization of the *Bos Taurus* β-*casein* gene," *Gene,* 1988, vol. 66, pp. 87-96.

Greenberg et al. "Characterization of a New Megakaryocytic Cell Line: The Dami Cell," *Blood,* 1988, vol. 72, No. 6, pp. 1968-1977.

Hong et al. "Inhibition of Protein Kinase C Suppresses Megakaryocytic Differentiation and Stimulates Erythroid Differentiation in HEL Cells," *Blood,* 1996, vol. 87, No. 1, pp. 123-131.

Martin "HEL Cells: A New Human Erythroleukemia Cell Line with Spontaneous and Induced Globin Expression," *Science,* 1982, vol. 216, pp. 1233-1235.

Ogura et al. "Establishment of a Novel Human Megakaryoblastic Leukemia Cell Line, MEG-01, With Positive Philadelphia Chromosome," *Blood,* 1985, vol. 66, No. 6, pp. 1384-1392.

Iyer et al. "The Automated Synthesis of Sufur-Containing Oligodeoxyribonucleotides Using 3H-1,2-Benzodithiol-3-one 1,1-Dioxide as a Sulfur-Transfer Reagent," *J. Org. Chem.,* 1990, vol. 55, pp. 4693-4699.

Woolf et al. "The stability, toxicity and effectiveness of unmodified and phosphorothioate antisense oligodeoxynucleotides in Xenopus oocytes and embryos," *Nucleic Acids Research,* 1990, vol. 18, No. 7, pp. 1763-1769.

Yu et al. "Attenuation of Serum Inducibility of Immediate Early Genes by Oncoproteins in Tyrosine Kinase Signaling Pathways," *Molecular and Cellular Biology,* 1993, vol. 13, No. 4, pp. 2011-2019.

Appleton & Lange, Critical Care Diagnosis & Treatment, Edited by Frederic S. Bongard and Darryl Y. Sue, Paramount Publishing Business and Professional Group.

PCR Protocols: A Guide to Methods and Applications, Edited by Michael A. Innis et al., Academic Press, Inc., 1990.

\* cited by examiner

Fig. 1

SIE
   5'-AGCTTCATTTCCCGTAAATCCCTAAGC
STAT1
   5'-CATGTTATGCATATTCCTGTAAGTG
MGFe
   5'-AGA<u>TTCTAGGAA</u>TTCAAATC
IRF-1 GAS
   5'-GCCTGA<u>TTCCCCGAAAT</u>GACGGCA
STAT3
   5'-GATCC<u>TTCTGGGAATT</u>CCTAGATC
STAT5/STAT6
   5'-GTA<u>TTTCCCAGAAA</u>GGAAC

METHOD FOR THE INHIBITION OF FUNCTION OF STAT TRANSCRIPTION FACTORS

[This patent application is a National Phase Concerning a Filing Under 35 U.S.C. 371, claiming the benefit of priority of PCT/US99/17366, filed Jul. 30, 1999, which claims the benefit of priority of U.S. Provisional Application Ser. No. 60/094,695, all of which are incorporated herein by reference] This application is a U.S. national stage application of international patent application No. PCT/US99/17366, filed Jul. 30, 1999, which claims the benefit of U.S. Provisional Application Ser. No. 60/094,695, filed Jul. 30, 1998.

GOVERNMENT SUPPORT

[This work was supported in part by grants from the US Public Health Service, the National Institutes of Health and the National Cancer Institute] This invention was made with government support under National Institutes of Health grant number NCI 5 R01 CA56072. The government has certain rights in the invention.

BACKGROUND OF THE INVENTION

1. Field of the Invention

The present invention relates to transcription factors, which induce the transcription of genes. More specifically, the present invention relates to a method of inhibiting transcription factors for use in the therapeutic treatment of disease associated with hyper-activated signal transduction pathways, particularly malignancy.

2. Description of Related Art

Transcription factors bind to specific DNA sequences, usually upstream from the coding region of a gene and affect the transcription of that particular gene. Signal transducers and activators of transcription (STAT) proteins comprise one family of transcription factors. Both for laboratory studies and for potential clinical use, interference with the function of specific transcription factors is a potentially powerful and highly selective way of inhibiting the activation of specific genes and of blocking cellular responses (e.g., cell proliferation, apoptosis, differentiation, activation).

The use of oligonucleotides as therapeutic agents may be able to interact specifically with individual or small numbers of target molecules to inhibit expression of disease-causing genes. For a review see Gewirtz et al (1998 Blood 92:712–736). Most of the attention has been placed on antisense oligonucleotides, DNA triplex-forming oligonucleotides, and ribozymes that are engineered to bind to specific DNA or RNA sequences and inhibit transcription or translation of the target gene. Generally examples of methods for inhibiting transcription factors that have been proposed include the following.

Small molecule pharmacologic agents might be utilized which interrupt signaling or metabolic pathways thus leading to activation of transcription factors. These agents have the disadvantage of non-specifically inhibiting other cellular molecules and functions and having non-specific toxic effects on cells.

Also, anti-sense oligonucleotides can be used. These molecules often have non-specific effects on the target DNA or RNA which are unrelated to their intended anti-sense inhibition of translation of mRNA. Significant inhibitory effects often are seen even with the control sense oligonucleotides.

A third method involves dominant-negative mutant transfections. This includes the transfection of cDNA encoding non-functional mutants of specific transcription factors or proteins that interact with the transcription factors. Such mutants are non-functional, and also interfere with the function of the normal endogenous transcription factor within the cells. These have the disadvantage of the technical difficulty of performing the transfections, isolating the cells that actually are expressing the dominant-negative protein, and regulating the level of expression of the dominant-negative protein in the cells.

It would therefore be useful to have a method for inhibiting transcription factors that does not have these disadvantages and can be used for both in vitro and in vivo use.

SUMMARY OF THE INVENTION

There is provided a method of modulating the function of a transcription factor by administering an effective amount of an oligonucleotide containing optimal nucleotide binding sites for the transcription factor. A therapeutic agent having an effective amount of an oligonuclotide for modulating function of transcription factors and a pharmaceutically acceptable carrier is also provided. There is provided oligonucleotides having transcription factor modulatory properties. Also provided is a treatment of patients having illnesses in which the activation of transcription factors play a role, by administering to a patient an effective amount of an oligonucleotide which competitively binds the related transcription factor. Also provided is a method of determining prognostic factors associated with particularly malignant cells by determining if particular transcription factors are constitutively activated.

DESCRIPTION OF THE DRAWINGS

Other advantages of the present invention will be readily appreciated as the same becomes better understood by reference to the following detailed description when considered in connection with the accompanying drawings wherein:

FIG. 1 shows the sequence of the sense strand of double-stranded DNA fragments that were used for gel mobility assays and for the inhibition of the activation of STAT5;

DETAILED DESCRIPTION OF THE INVENTION

Figure 2:
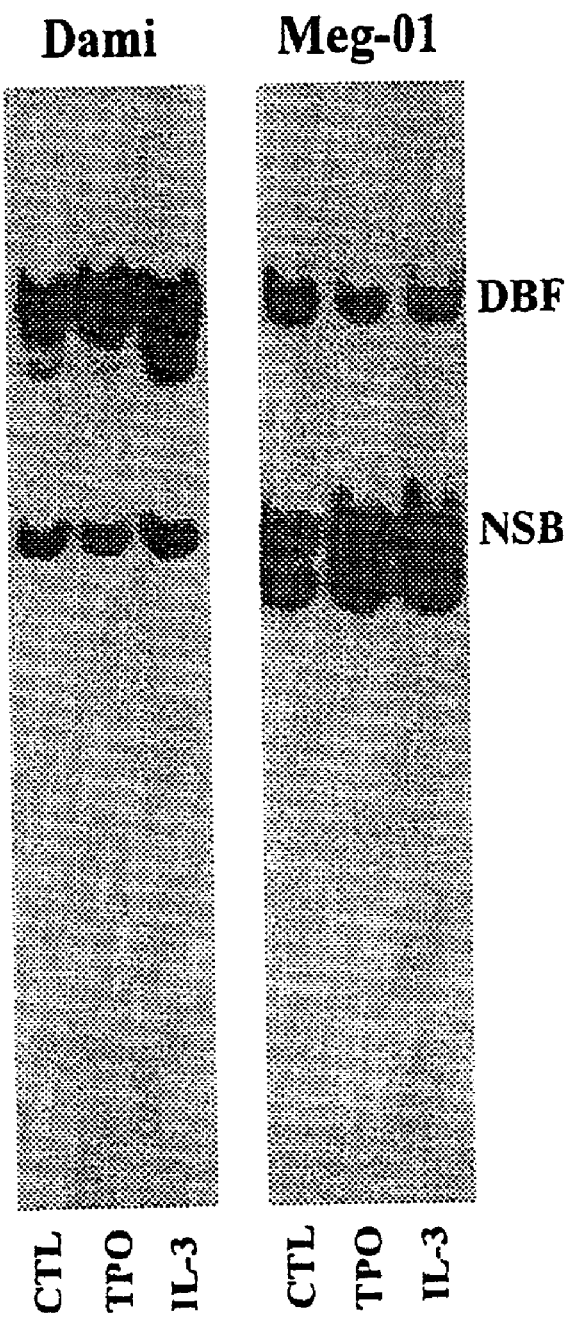
FIG. 2 shows the constitutive activation of a STAT-like DNA-binding factor in Dami/HEL and Meg-01 cells; Nuclear extracts from each cell line cultured in the absence of cytokine (CTL) or in the presence of as much as 400 ng/ml TPO or 40 ng/ml IL-3, were incubated with [$^{32}$P]-labeled, double-stranded IRF-1 GAS (SEQ ID NO. 2) oligonucleotide; The DNA-binding complex and unbound probes were separated electrophoretically on 5% non-denaturing polyacrylamide gels; The autoradiograph shows the STAT-like DNA-binding factor (DBF) and the nonspecific bands (NSB)

Generally, the present invention relates to a method of inhibiting the function of transcription factors in viable cells, using specific, double-stranded oligonucleotides that contain the optimal nucleotide binding site(s) recognized by a given transcription factor. This method is applicable in vitro for inhibiting DNA binding and function of any transcription factor that targets a specific nucleotide sequence to which it binds on native, endogenous DNA to exert its transcriptional activation function. The method can also use a specific nucleotide sequence which represents a consensus sequence of the targeted DNA upon which the transcription factor acts. Some examples of such transcription factors include (but are not limited to) the STAT family (STATs 1, 2, 3, 4, 5a, 5b, and 6), fos/jun, NF kappa B, HIV-TAT, and the E2F family.

The present invention provides a method of inhibiting the function of transcription factors as shown in the Example herein.

Contrary to that used in the art, i.e. antisense oligonucleotides, DNA triplex-forming oligonucleotides, and ribozymes that are engineered to bind to specific DNA or RNA sequences, the present invention uses double-stranded oligonucleotides that contain, for example, the consensus STAT5 binding site, TTCNNNGAA, to competitively inhibit the ability of activated STAT to bind to its endogenous DNA targets.

As shown in the Examples, the applicants have discovered that growth factor independent leukemia cells have a constitutively activated STAT-like DNA-binding factor (DBF). The STAT-like DBF was found to be STAT5. If was also discovered that constitutive activation of STAT5 correlates with cell proliferation. Furthermore the applicants found that cell proliferation could be inhibited by blocking STAT5 transcription factor using a double-stranded oligonucleotide containing the STAT5 binding sequence AGATTTCTAGGAATTCAAATC (SEQ ID NO:1) or GCCTGATTTCCCCGAAATGACGGCA (SEQ ID NO:2) or GTATTTCCCAGAAAAGGAAC (SEQ ID NO:3), which contain the STAT5 consensus binding site TTCNNNGAA, in which "N" means any nucleotide. This oligonucleotide with the STAT5 binding sequence penetrates into cells and serves as a competitive inhibitor that binds to activated STAT5 in the cells. Oligonucleotide bound, activated STAT5 is not available to bind to endogenous DNA at STAT5 binding sites and therefore cannot function, i.e., activate the transcription of various cellular genes. Inhibiting the synthesis of protein by this method can have many effects on cells. In the current invention the inhibition of STAT5 function in this manner, prevented cell proliferation and led to the death of human leukemic cells in vitro. Hence, the data is highly predictive of the present invention being effective against human malignant cells.

Studies have shown that there is constitutive activation of transcription factors, such as STAT3 and STAT5, in human malignant cell lines in vitro and in primary malignant cells obtained from fresh human neoplasms as diverse as acute myeloid leukemias, chronic myeloid leukemias, head and neck carcinomas and breast carcinomas. Activated transcription factors are most critical in continuously dividing cells and during the process of cell division. This indicates a favorable therapeutic index, since malignant cells are continuously dividing and would be most affected while normal cell populations having a lower proliferative index would be less exposed to the oligonucleotide's inhibitory effect.

In the case of many transcription factors, activation is not critical to normal cellular functions, even though it may be critical to continued malignant cell survival and proliferation. For example, mice in which both the STAT5a and STAT5b genes have been knocked out are viable and survive to adulthood, suggesting that STAT5 is not essential. Thus, inhibition of activated STAT5 in an acute leukemia patient has a significant therapeutic effect, and almost no toxic effect. Any neoplastic disease in which there is an activated transcription factor, which is critical to maintaining survival and proliferation of the malignant cells is a target for this therapeutic approach.

Additionally, the inflammation and tissue destruction in many immunologic and inflammatory disorders are driven primarily by cytokines, such as tumor necrosis factor (TNF)-, which acts largely through activation of the transcription factor, NF kappa B. Thus, the sequence-specific, double-stranded oligonucleotide containing the consensus binding site, GGGGACTTTCCC (SEQ ID NO:4), for example the oligonucleotide having the sequence AGTTGAGGGGACTTTCCCAGGC (SEQ ID NO:5) is effective in interfering with the transcriptional activating function of NF kappa B and blocks the inflammatory response that causes the tissue destruction in such diverse diseases as rheumatoid arthritis, and acute pancreatitis.

Bacterial sepsis has an extremely high morbidity rate. Most evidence shows that much of the sepsis syndrome is caused by endotoxin-mediated stimulation of cytokines, which in turn lead to inflammatory and vascular effects. Again, since most pro-inflammatory cytokines result in activation of transcription factors such as STATs and NF kappa B, acute treatment with specific double-stranded oligonucleotides designed to competitively inhibit the function of these transcription factors is a rapid and effective means of interfering with the cytokine-mediated events responsible for the major complications of bacterial sepsis.

Recently, Angiotensin II has been shown to activate the JAK2/STAT5 signal transduction pathway in cardiac myocytes. In addition, angiotensin-converting enzyme (ACE) inhibitory drugs have been shown to be an effective clinical treatment in the immediate post-myocardial infarction period, showing that angiotensin II inhibition is beneficial in this pathologic condition. Thus, STAT5 activation as a result of excessive angiotensin II production contributes to the morbidity and mortality of myocardial infarction. Therefore, a novel therapeutic approach in the early post-infarction period is the use of a STAT5-binding, double-stranded oligonucleotide as a short-term inhibitor of STAT5 activation.

Also provided by the present invention are therapeutics and pharmaceutical compositions for use in the treatment of patients having illnesses in which activation of transcription factors play a role. The treatment consists of administering to a patient an effective amount of an oligonucleotide which competitively binds a transcription factor of the related illness. These therapeutics and pharmaceuticals which are utilized contain an effective amount of an oligonucleotide for modulating the function of transcription factors and a pharmaceutically acceptable carrier. More specifically, there is provided a pharmaceutical composition for inhibiting a transcription factor in a cell. The pharmaceutical composition contains therein an effective amount of a double stranded oligonucleotide, the oligonucleotide having a sequence bound by a transcription factor.

The composition and therapeutic of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the therapeutic, composition and method of treatment of the present invention, the compounds of the present invention can be administered in various ways. It should be noted that it can be administered as the compounds or as a pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intra-arterial, intramuscular, intra-peritoneally, and intra-nasal administration as well as through intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The above discussion provides a factual basis for the use of transcription factor inhibitors. The methods used with and the utility of the present invention can be shown by the following non-limiting examples and accompanying figures.

EXAMPLES

General Methods:

General methods in molecular biology: Standard molecular biology techniques known in the art and not specifically described are generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Polymerase chain reaction (PCR) is carried out generally as in *PCR Protocols: A Guide To Methods And Applications*, Academic Press, San Diego, Calif. (1990). Reactions and manipulations involving other nucleic acid techniques, unless stated otherwise, are performed as generally described in Sambrook et al., 1989, *Molecular Cloning: A Laboratory Manual*, Cold Spring Harbor Laboratory Press, and methodology as set forth in U.S. Pat. Nos. 4,666,828; 4,683,202; 4,801,531; 5,192,659 and 5,272,057 and incorporated herein by reference. In-situ (In-cell) PCR in combination with Flow Cytometry can be used for detection of cells containing specific DNA and mRNA sequences (Testoni et al, 1996, Blood 87:3822.)

General methods in immunology: Standard methods in immunology known in the art and not specifically described are generally followed as in Stites et al. (eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

Nuclease Resistance:

Nuclease resistance for the oligonucleotides of the present invention, where needed, is provided by any method known in the art that does not substantially interfere with biological activity of the oligodeoxynucleotides as needed for the method of use and delivery [Iyer et al., 1990; Radhakrishnan, et al., 1990; Eckstein, 1985; Spitzer and Eckstein, 1988; Woolf et al., 1990; Shaw et al., 1991] and which do not produce appreciable toxicity. Modifications that can be made to the oligonucleotides in order to enhance nuclease resistance include modifying the phosphorous or oxygen heteroatom in the phosphate backbone, short chain alkyl or cycloalkyl intersugar linkages or short chain heteroatomic or heterocyclic intersugar linkages. These include preparing methyl phosphonates, phosphorothioates, phosphorodithioates and morpholino oligomers. In one embodiment it is provided by having phosphorothioate bonds linking between the four to six 3'-terminus nucleotide bases. Alternatively, phosphorothioate bonds link all the nucleotide bases. Phosphorothioate oligonucleotides do not normally show significant toxicity at concentrations that are effective and exhibit sufficient pharmacodynamic half-lives in animals [Agarwal et al., 1996] and are nuclease resistant. Other modifications known in the art may be used where the biological activity is retained, but the stability to nucleases is substantially increased and toxicity not significantly increased.

The present invention also includes all analogues of, or modifications to, an oligonucleotide of the invention that does not substantially affect the transcription factor binding function of the oligonucleotide. Such substitutions may be selected, for example, in order to increase cellular uptake or for increased nuclease resistance as is known in the art. The term may also refer to oligonucleotides which contain two or more distinct regions where analogues have been substituted.

The nucleotides can be selected from naturally occurring or synthetically modified bases. Naturally occurring bases include adenine, guanine, cytosine, thymine and uracil. Modified bases of the oligonucleotides include xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thioalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, analogues of nucleotides can be prepared wherein the structure of the nucleotide is fundamentally altered and that are better suited as therapeutic or experimental reagents. An example of a nucleotide analogue is a peptide nucleic acid (PNA) wherein the deoxyribose (or ribose) phosphate backbone in DNA (or RNA) is replaced with a polyamide backbone which is similar to that found in peptides. PNA analogues have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides is include polymer backbones, morpholino polymer backbones [U.S. Pat. No. 5,034,506], cyclic backbones, or acyclic backbones, sugar mimetics or any other modification including which can improve the pharmacodynamics properties of the oligonucleotide.

The oligonucleotides and ribozymes of the present invention can be synthesized by any method known in the art for ribonucleic or deoxyribonucleic nucleotides. For example, the oligonucleotides can be prepared using solid-phase synthesis such as in an Applied Biosystems 380B DNA synthesizer. Final purity of the oligonucleotides is determined as is known in the art.

Delivery of Therapeutics (Compound):

The therapeutic compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice or other experimental animals exemplified herein which treatment has a length proportional to the length of the disease process and drug effectiveness. The doses may be single doses or multiple doses over a period of several days, but single doses are preferred.

The doses may be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224;

4,439,196; and 4,475,196. Many other such implants, delivery systems, and modules are well known to those skilled in the art.

A pharmacological formulation of the compound utilized in the present invention can be administered orally to the patient. Conventional methods such as administering the compounds in tablets, suspensions, solutions, emulsions, capsules, powders, syrups and the like are usable. Known techniques which deliver it orally or intravenously and retain the biological activity are preferred.

In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered will vary for the patient being treated and will vary from about 100 ng/kg of body weight to 100 mg/kg of body weight per day and preferably will be from 10 µg/kg to 10 mg/kg per day.

Example 1

Reagents

Recombinant human thrombopoietin (TPO), interleukin (IL)-3, IL-6, and granulocyte macrophage colony-stimulating factor (GM-CSF) were purchased from PeproTech (Rocky Hill, N.J.). Anti-IL-3 and anti-TPO neutralizing antibodies were purchased from R & D system (Minneapolis, Minn.). Anti-phosphotyrosine antibody-agarose and anti-JAK2 antiserum were purchased from Upstate Biotechnology (Lake Placid, N.Y.). Phosphotyrosine western blotting kit (chemiluminescence) was purchased from Boehringer Mannheim Biochemicals (Indianapolis, Ind.). Anti-goat IgG and anti-mouse IgG antibodies labeled with fluorescein isothiocyanate were purchased from Zymed (South San Francisco, Calif.). Anti-STAT1, -STAT2, -STAT3, -STAT4, -STAT5 and -STAT6 antibodies were purchased from Santa Cruz Biotechnology (Santa Cruz, Calif.). [Methyl-$^3$H]-thymidine ([$^3$H]-TdR; Specific activity 70–86 Ci/mmol) and [P]-dATP (specific activity >3000 µCi/mmol) were purchased from Amersham Life Science (Arlington Heights, Ill.).

Cell lines

Human megakaryocytic leukemic cell line, HEL/Dami, originally described by Greenberg et al (1988 Blood 72:1968), was obtained from American Type Culture Collection (ATCC) and was maintained in Iscove's Modified Dulbecco's Medium (IMDM; GIBCO-BRL, Grand Island, N.Y.) containing 10' horse serum or sera-free nutridoma HEL. Recently, ATCC and DSMZ (German Collection of Microorganisms and Cell Cultures) have determined that all samples of the HEL/Dami cell line that were available for them to analyze were genetically and karyotypically identical to the human erythroleukemia cell line (HEL) described previously (Martin 1982 Science 216:1233), which has both erythroid and megakaryocytic characteristics (Hong 1996 Blood 87:123), for clarity refered to herei as Dami/HEL. Human megakaryoblastic leukemic cell line, Meg-01, originally described by Ogura et al (1985 Blood 66:1384), was obtained from ATCC and was maintained in RPMI 1640 medium (GIBCO-BRL) with 10% heat-inactivated fetal bovine serum (FBS). Human factor-dependent megakaryoblastic cell line, Mo7e, originally described by Avanzi et al (1988 Br J Haematol. 69:359), was obtained from Genetics Institute (Boston, Mass.) and was maintained in IMDM medium with 10% FBS, 1% L-glutamine and 5 ng/ml GM-CSF. All the cells were incubated at 37° C. in a fully humidified atmosphere with 5% $CO_2$ in medium alone or in the presence of various concentrations of cytokines. In experiments to detect the effects of known cytokines or potential cytokines in Dami/HEL or Meg-01 conditioned media, Mo7e cells were prepared by washing three times with medium and starved for 18 hours in medium without growth factors prior to cytokine or conditioned medium treatments, as described by Dusanter-Fourt et al (1994 EMBO J. 13:2583). Dami/HEL cells were cultured in IMDM without serum but with 1× Nutridoma HU (Boehringer Mannheim Biochemicals, Indianapolis, Ind.), and Meg-01 cells in RPMI 1640 with 1× Nutridoma-HU in experiments in which cytokine production and specific cytokine effects were being studied.

Effects of Cytokines on Cell Growth

To determine the proliferative response of cells to cytokines, DNA synthesis was measured by [$^3$H]-TdR incorporation. The assays were performed in triplicate, using $4 \times 10^5$ cells for Mo7e and Meg-01, or $2 \times 10^5$ cells for Dami/HEL cells. Mo7e cells in IMDM with 10% FBS, and Dami/HEL and Meg-01 cells in medium with 1× Nutridoma HU were cultured for 72 hours without or with cytokines. Subsequently, the cells were labeled with 2 µCi/ml of [$^3$H]-TdR for an additional 4 hours. Incorporation of [$^3$H]-TdR into newly synthesized DNA (counts per minute; CPM) was determined by liquid scintillation counting, according to a previously described protocol (Lui 1992 Cancer Res, 52:3667). For the analysis of cell ploidy, cytokine-starved Mo7e cells ($1 \times 10^6$ cells/ml) were cultured in IMDM medium with 10% FBS plus growth factors. Dami/HEL and Meg-01 cells $1 \times 10^6$/ml) were cultured in medium with 1× Nutridoma-HU plus growth factors, at 37° C. for 1 to 10 days. The treated cells were harvested on day 3, 5, 7 and 10. The DNA content of the cells was quantitated with a FACScan flow cytometer (Becton Dickson, Rutherford, N.J.), following a published is protocol (Taylor 1980 J Histochem Cytochem 28:1021. Isolated human lymphocytes were used as a diploid control.

Immunoprecipitation and Western Blotting

Unstimulated or cytokine-stimulated cells were lysed in modified RAPI buffer with 1% NP-40, and extracts were immunoprecipitated, as described (Dusanter-Fourt 1994). The detergent-soluble proteins were incubated with anti-phosphotyrosine agarose for 3 hours at 4° C. with shaking. The immunoprecipitates were washed four times with modified RAPI buffer, lysed in SDS buffer and separated by 7.5 k non-reducing sodium dodecyl sulfate-polyacrylamide gel electrophoresis (SDS-PAGE). Proteins then were transferred to nitrocellulose membrane and probed sequentially with rabbit anti-JAK2 antibody and anti-rabbit IgG antibody labeled with peroxidase. Phosphorylated JAK2 was visualized with enhanced chemiluminescence techniques according to the manufacturer's recommended procedure. For the detection of tyrosine phosphorylation of MAPK and other cellular proteins, cells treated with or without cytokines were lysed in SDS buffer, and 30 µg of protein was loaded in each sample lane for 7.5% SDS-PAGE. The SDS-PAGE-separated proteins were transferred to PVDF membranes and probed with an anti-phosphotyrosine antibody kit (Boehringer Mannheim, Indianapolis, Ind.) or with the Phospho-Plus MAPK antibody kit (New England Biolabs, Beverly, Mass.).

Preparation of Nuclear Extracts and Gel Mobility Shift Assays

Preparation of nuclear extracts and gel mobility shift assays were performed according to methods described previously (YL 1993 Mol Cell Biol 13:2011). Briefly, equal amounts of nuclear proteins (5–10 μg) for each sample were incubated for 30 minutes at 30° C. with 10,000 dpm of [$^{32}$P]-labeled double-strand DNA fragment (IRF-1 GAS), which contains the interferon-γ activation site (GAS) that binds to interferon regulatory factor (IRF-1) (5'-GCCT-GATTTCCCCGAAATGACGGCA)SEQ ID NO. 2 (GORO-DETSKY 1988 GENE 66:87), which contains an identical sequence to that of Bovine mammary gland factor element (MGFe), TTCCCCGAA SEQ ID NO 6. For competition assays, unlabeled FIRE, (5'-AGCGCCTCCCCGGCCGGG-GAG) SEQ ID NO 7, interferon-stimulated response element (ISG15 ISRE; 5'-GATCGGGAAAGGGAAAC-CGAAACTGAAGCC) SEQ ID NO 8, and sis-inducible element (SIE, 5'-AGCTTCATTTCCCGTAAATC-CCTAAGC) SEQ ID NO 9 also were used as potential DNA-protein binding competitors, by adding 50× molar excess of each unlabeled DNA fragment, along with the [$^{32}$P]-labeled IRF-1 GAS (SEQ ID NO. 2) oligonucleotide probe. Unlabeled MGFe (SEQ ID NO. 1) was used as a specific competitor for STAT5 binding to IRF-1 GAS (SEQ ID NO. 2). For gel mobility supershift assays, nuclear extracts were co-incubated with the indicated specific anti-STAT antibodies and the [$^{32}$P]-labeled oligonucleotide probes. The DNA-protein complexes and unbound probe were separated electrophoretically on 5% native polyacrylamide gels in 0.5×TBE buffer (44.5 mM Tris, pH 8.0, 1 mM EDTA and 4455 mM boric acid) for 3 hours constant 140 volts. The gels were fixed and dried, and the DNA-protein complexes were visualized by autoradiography at −70° C. with Kodak X-OMAT film and a DuPont Cranex lightning-plus intensifying screen.

Reverse Transcription/Polymerase Chain Reaction (RT/PCR)

Cellular mRNA was prepared with RNAzol™ (Cinna/Bio Tecx Lab, Houston, Tex.) following the protocol suggested by the manufactures. A primer set (TransPrimers, Calbiochem, Calif.) was used to check rearranged BCR/ABL transcripts. RT/PCR for normal c-ABL also was performed to check RNA quality. A RNA PCR Core kit (GeneAmp, Perkin Elmer, Branchburg, N.J.) was used to perform RT/PCR following the manufacturer's protocol. A 1.8% agarose gel was used for electrophoretic analysis of the PCR products. RT/PCR was performed at least twice to confirm the findings.

Bioassays of Stimulatory Cytokines

Factor-independent Dami/HEL and Meg-01 cells were examined for the capacity to produce autocrine cytokines. Mo7e cells, the survival of which depends on the presence of any of several growth factors, including GM-CSF, IL-3, IL-6, IL-9, TPO, steel factor/c-kit ligand and TNF-α, were used as a bioassay system to detect possible stimulatory factors that might be produced by Dami/HEL or Meg-01 cells. Conditioned medium was prepared by collecting supernatants from 3-day cultures of Dami/HEL or Meg-01 cells grown in serum-free conditions. The conditioned medium was incubated with freshly prepared Mo7e cells for 72 hours and cell proliferation was determined by [$^3$H]-TdR incorporation into DNA, following the procedure described in the prior section. If Mo7e-stimulating activity is detected in the medium, it would imply that the factor-independent cell lines may produce and secrete autocrine stimulatory factor(s). If no Mo7e proliferation-stimulating activity of the conditioned medium is detected, the involvement of humoral factors in the factor-independent growth of Dami/HEL and Meg-01 cells is reduced substantially.

Human Megakaryocytic Leukemic Cell Lines Dami/HEL and Meg-01 Cells Grow in a Factor-Independent Manner To determine effects of cytokines on DNA synthesis of the proliferating cells, various concentrations of cytokines were incubated with Dami/HEL, Meg-01, and Mo7e cells for 3 days and labeled subsequently with [$^3$H]-TdR for the final is four hours of culture. When 0–200 ng/ml of TPO was incubated with the cytokine-independent cell lines, Dami/HEL and Meg-01, no significant stimulation of [3H] incorporation was observed. The cells also were tested f or their response to other cytokines, including GM-CSF, IL-3, IL-6 and TNF-α, and neither Dami/HEL nor Meg-01 cell proliferation is affected by any of these cytokines. Addition of anti-IL-3 or anti-TPO neutralizing antibodies did not inhibit [$^3$H]-TdR incorporation or cell proliferation. However, when factor-dependent Mo7e cells were incubated with various concentration of TPO, incorporation of [$^3$H]-TdR was stimulated significantly, in a dose-dependent manner. At the concentration of 50 ng/ml, TPO regularly stimulates the incorporation of [$^3$H]-thymidine 4.5-fold over that of control Mo7e cells at 3 days. IL-3, GM-CSF, IL-6, and TNF-α also stimulated Mo7e cell proliferation.

To investigate effects of cytokines on the maturation of these megakaryocytic leukemic cell lines, the cells were stained with propidium iodide, and cell ploidy was analyzed by a FACscan flow cytometer. In the untreated control Dami/HEL, Meg-01 or Mo7e cells, the majority of cells were diploid. When the cells were incubated with 100–400 ng/ml of TPO for 1–10 days, no significant increase of cell ploidy was observed in any of these cell lines.

STAT-Like DNA-Binding Factors are Activated Constitutively in Dami/HEL and Meg-01 Cells Applicants analyze STAT DNA-binding factor activation by gel electrophoretic mobility shift assays (EMSA) with a [$^{32}$P]-labeled oligonucleotide containing the IRF-1 GAS (SEQ ID NO. 2) consensus STAT binding site, as the probe. DNA-binding protein(s) were detected in the nuclear extracts from Dami/HEL and Meg-01 cells in the absence cytokine exposure (FIG. 2). Addition of as much as 400 ng/ml of TPO or 40 ng/ml IL-3 does not have any further effect on the constitutive DNA-binding protein activity in these growth factor-independent cell lines (FIG. 2). Exposure of these cells to GM-CSF, IL-6, EPO or TNF-α also did not result in significant enhancing or inhibitory effects on the constitutive DNA-binding factor activity. In contrast, no STAT-like DNA-binding factor was detectable in untreated control cells.

Figure 4:
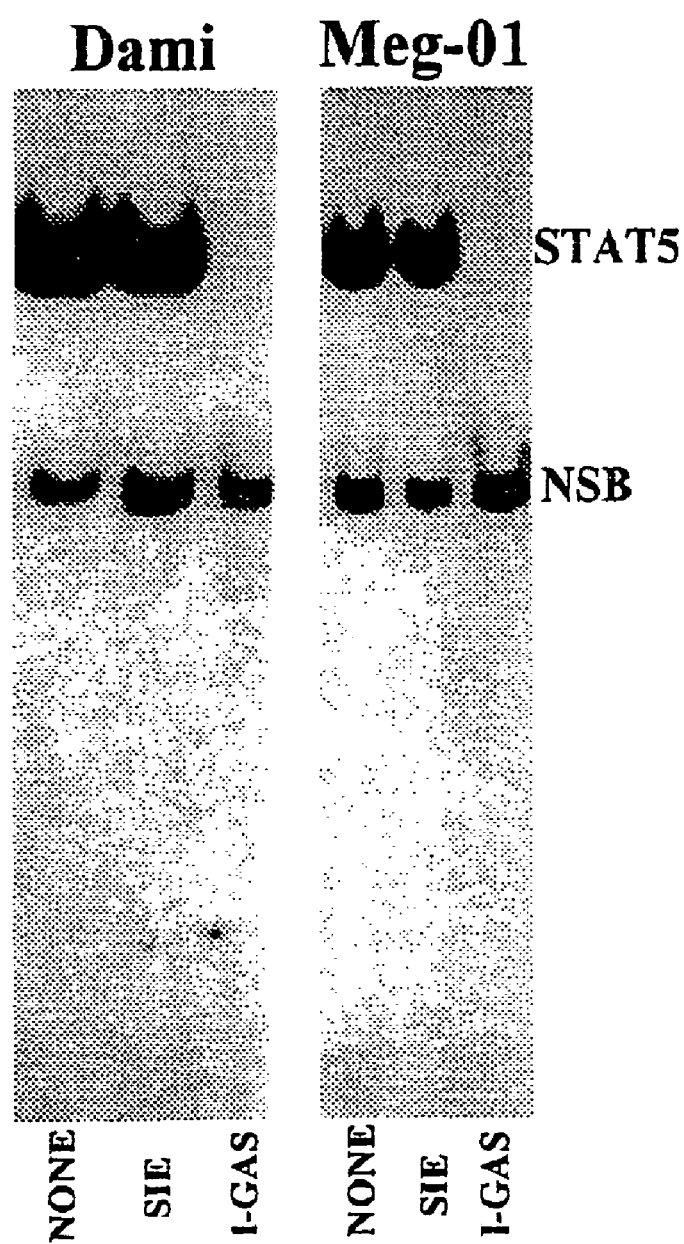
FIG. 4 shows the effects of IRF-1 GAS (SEQ ID NO. 2) on the binding of STAT 5 to the [$^{32}$P]-labeled MGFe (SEQ ID NO. 1); Nuclear extracts from HEL/Dami and Meg-01 cells were incubated with the [$^{32}$P]-labeled MGFe probe (SEQ ID NO. 1) without IRF-1 GAS (NONE) (SEQ ID NO. 2) or with [$^{32}$P]-labeled probe plus a 100-fold excess of unlabeled oligonucleotide SIE (SEQ ID NO. 9) or IRF-1 GAS (1-GAS) (SEQ ID NO. 2), respectively; The DNA binding complexes were separated in a 5% non-denaturing polyacrylamide gel; The autoradiograph shows the STAT transcription factor (STAT5) and nonspecific bands (NSB)
Figure 5:
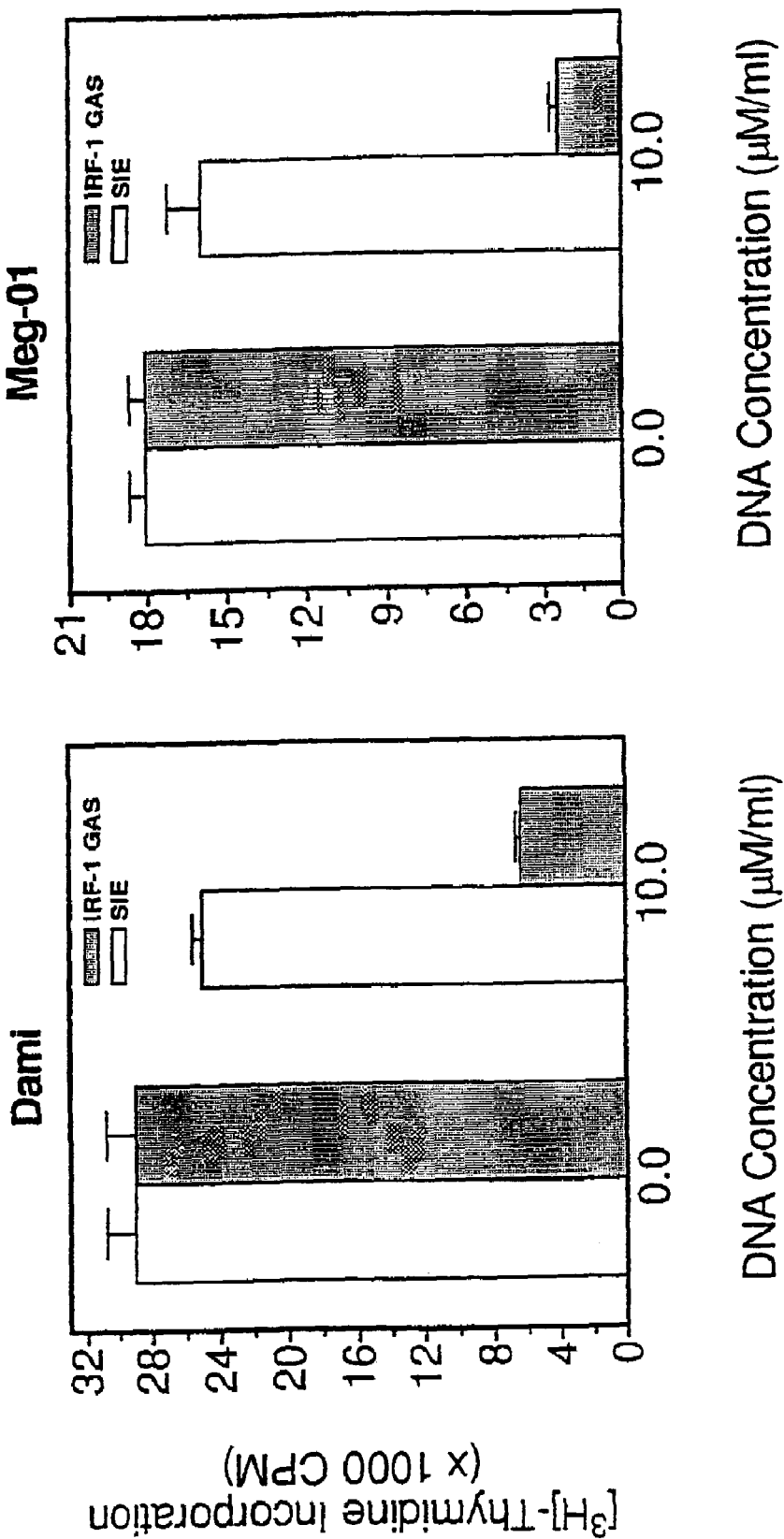
FIG. 5 shows the effects of IRF-1 GAS double-stranded oligonucleotide (SEQ ID NO. 2) on HEL/Dami and Meg-01 cell survival and proliferation; HEL/Dami and Meg-01 cells were incubated with the indicated concentrations of IRF-1 GAS oligo (SEQ ID NO. 2) or SIE control oligo (SEQ ID NO. 9) with lipid for 72 hours and labeled with 2 $\mu$Ci/ml [$^3$H]-thymidine (TdR); TdR incorporation into newly synthesized DNA was determined by counting the radioactivity (CPM) from triplicate samples and expressed as the mean CPM.
Figure 6:
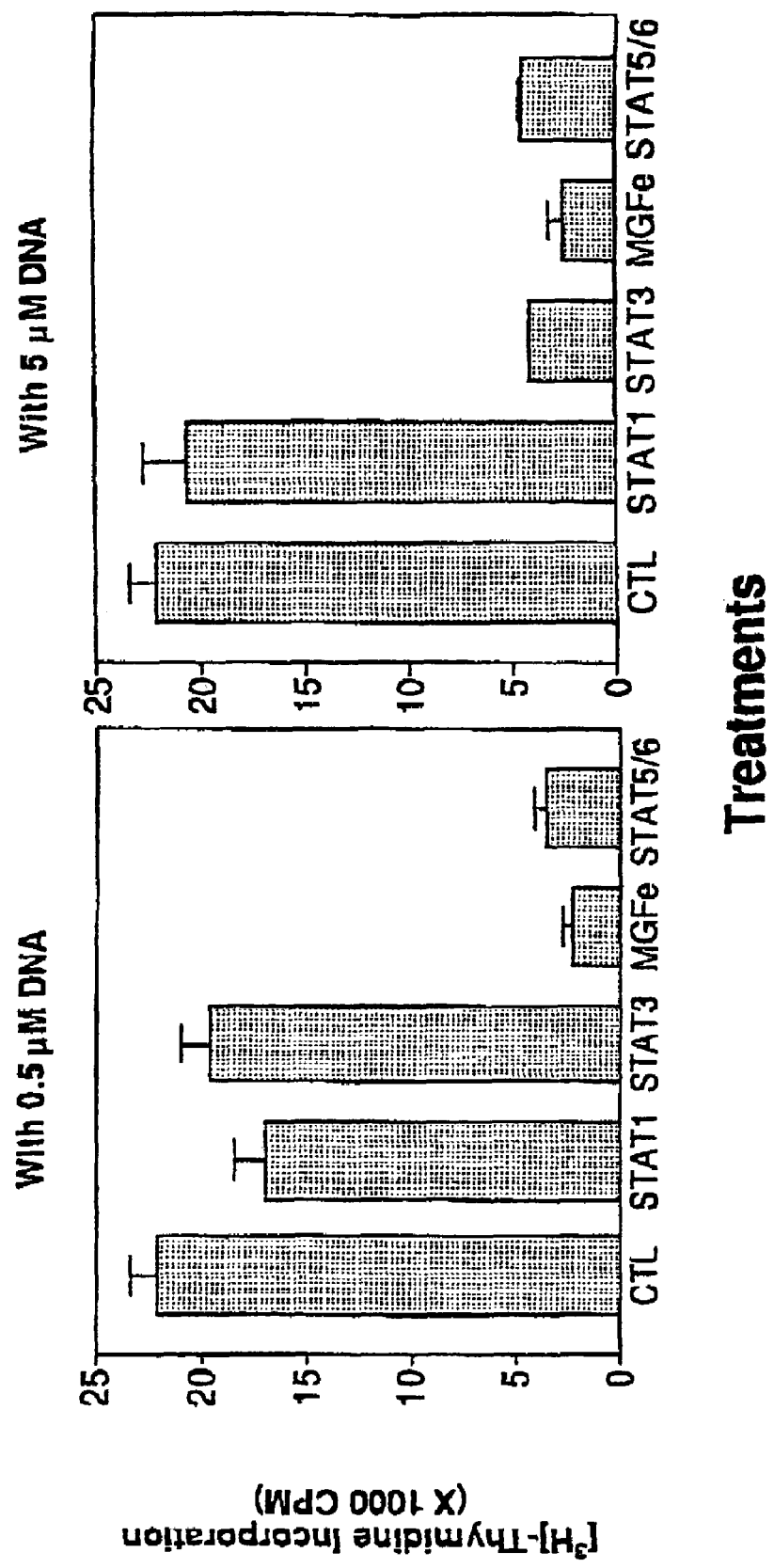
FIG. 6 shows the effects of IRF-1 GAS double-stranded oligonucleotide (SEQ ID NO. 2 on HEL/Dami cell survival and proliferation; HEL/Dami cells were incubated with the indicated concentrations on STAT1 (SEQ ID NO. 10), STAT3 (SEQ ID NO. 11), MGFe (SEQ ID NO. 1), STAT5/6 (SEQ ID NO. 3) oligo or no oligo control (CTL) with lipid for 72 hours and labeled with 2 $\mu$Ci/ml [$^3$H]-thymidine (TdR); TdR incorporation into newly synthesized DNA was determined by counting the radioactivity per minute (CPM) from triplicate samples and expressed as the mean CPM.

The Constitutive and Cytokine-Activated STAT-Like Factor Binds Specifically to DNA Containing the IRF-1 GAS Sequence Experiments were performed to identify the specific STAT protein activated in these megakaryocytic leukemic cell lines. First, using a set of oligonucleotides to attempt to inhibit competitively the binding of the STAT-like factor to [$^{32}$P]-labeled IRF-1 GAS (SEQ ID NO. 2). When Dami/HEL and Meg-01 nuclear extracts were co-incubated with the labeled MGFe probe (SEQ ID NO. 1) plus a 100-fold molar excess of unlabeled SIE (SEQ ID NO. 9) or IRF-1 GAS (SEQ ID NO. 2) (FIG. 4) or FIRE (SEQ ID NO. 7) or ISRE SEQ ID NO. 8) oligonucleotides, which do not contain TTCCCCGAA sequence, no competitive inhibition or the formation of DNA-protein complexes was observed. However, a 50-fold molar excess of the unlabeled MGFe (SEQ ID NO. 1, which contains the same TTCCCCGAA STAT-binding sequence as IRF-1 GAS (SEQ ID NO. 2), completely abolished the formation of the labeled DNA-protein complexes. Similar results were found with Meg-01.

When the nuclear extracts from TPO-treated Mo7e cells were incubated with {$^{32}$P}-labeled IRF-1 GAS (SEQ ID NO. 2) probe or the [$^{32}$P]-labeled probe plus a 50-fold molar excess of unlabeled FIRE (SEQ ID NO. 7), ISRE (SEQ ID NO. 8), SIE (SEQ IN NO. 9) or MGFe(SEQ ID NO. 1) oligonucleotides, the cytokine-induced DNA-binding factor in Mo7e cells had the same features as the constitutive activated STAT-like factor in Dami/HEL cells. Both of the factors are able to bind to the IRF-1 GAS (SEQ ID NO. 2) probe, and their binding activity could be abolished completely by in labeled MGFe (SEQ ID NO. 1), but not by oligonucleotides that do not contain the TTCNNNGAA sequence.

The Constitutively Activated IRF-1 GAS-Binding Factor Activated in the Dami/HEL and Meg-01 Cells, and the Cytokine-Induced IRF-1 GAS-Binding Factor Identified in Mo7e Cell Lines is STAT5

Figure 3:
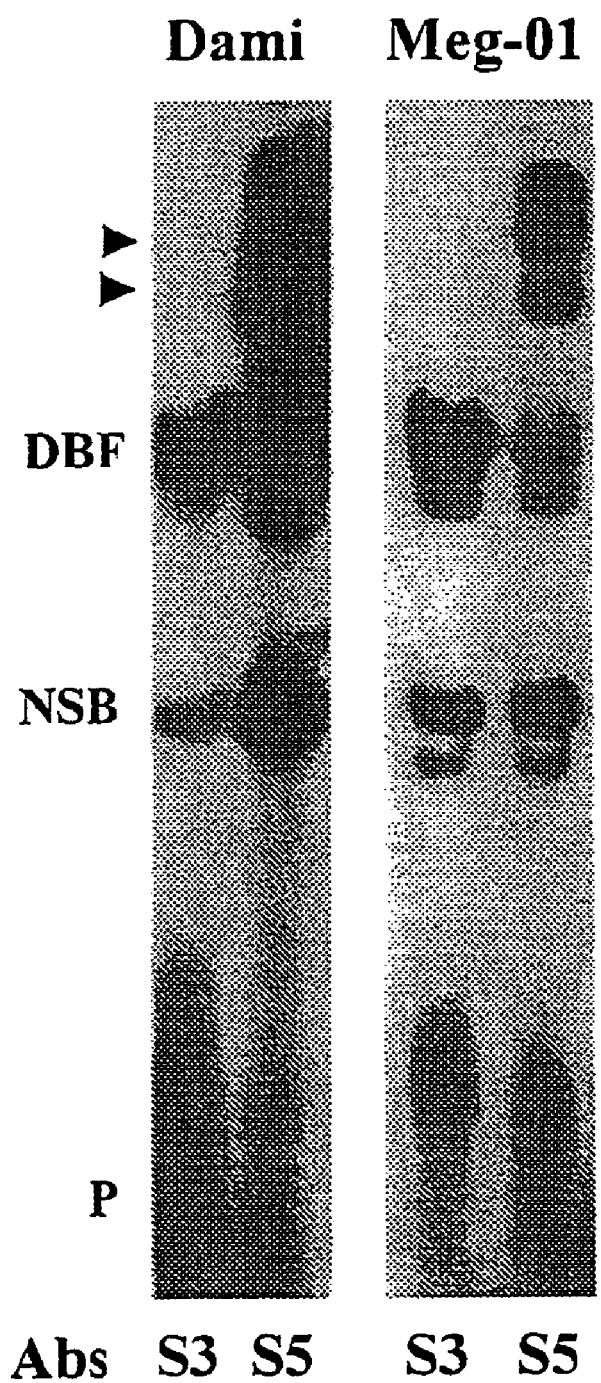
FIG. 3 shows the identification of the constitutively activated DNA-binding factor in HEL/Dami and Meg-01 cells by gel electrophoretic mobility supershift assays; Nuclear extracts from HEL/Dami and Meg-01 cells without cytokine exposure were incubated with the [$^{32}$P]-labeled MGFe probe (SEQ ID NO. 1) plus anti-STAT3 antiserum (S3), or with the [$^{32}$P]-labeled probe plus anti-STAT5 antiserum (S5); The autoradiograph shows the STAT DNA-binding factor (DBF), nonspecific bands (NSB) and free IRF-1 GAS probe (P) (SEQ ID NO. 2); The arrowheads indicate the supershifted complexes, these results are representative of three separate experiments; Nuclear extracts also were incubated with the [$^{32}$P]-labeled MGFe probe (SEQ ID NO. 1) plus anti-STAT1, anti-STAT2 and anti-STAT6 antiserum, no supershifted complexes were observed.

To identify the specific DNA-binding factor(s), gel mobility supershift assays with antibodies to specific STAT proteins were used to examine the type of STAT(s) involved in the DNA-protein complexes. When anti-STAT5 antiserum was used, supershift of the DNA-protein complexes was observed with nuclear extracts from Dami/HEL and Meg-01 cells cultured in medium without cytokines (FIG. 3) or from TPO-treated Mo7e cells, but not in untreated Mo7e cells. However, when anti-STAT3 antiserum was used, no supershift of DNA-protein complexes occurred in TPO-treated Mo7e or unstimulated Dami/HEL or Meg-01 cells (FIG. 3). Reactions of the DNA-protein complexes with anti-STAT1, anti-STAT2, anti-STAT4 and anti-STAT6 antibodies also were investigated, and no supershifted DNA-protein complexes were observed. These results indicate that the predominant or exclusive constitutively activated (in Dami/HEL and Meg-01 cells) or cytokine-induced (in Mo7e cells) STAT DNA-binding factor in these megakaryocytic leukemic cell lines is STAT5.

The JAK2/STAT5 signal transduction pathway is activated constitutively in the growth factor-independent megakaryocytic cell lines, Dami/HEL and Meg-01. In contrast, the activation of this signaling pathway is strictly cytokine-induced in the growth factor-dependent megakaryocytic cell line, Mo7e. STAT-related transcription factors are activated constitutively in primary cells from acute leukemia patients, and as shown in the present invention the close relationship between cell proliferation and the activation of JAK2/STAT5, constitutive activation of the JAK2/STAT5 pathway is believed to be one of the important mechanisms of leukemogenesis and of maintaining the leukemic phenotype. The STAT signaling pathway may also contribute to onco-genesis.

The accumulated data shows that aberrant expression or mutational activation of cytokine receptors or their downstream signal transduction pathways have an important role in abnormally, constitutively activated signal transduction pathways and in factor-independent cell growth.

Specific competitive inhibition of activated STAT5 prevented the constitutively activated STAT5 from inducing proliferation of these malignant, leukemic cell lines and resulted in death of the leukemic cells.

Specific oligodeoxynucleotide sequences are known to be preferential binding sites for specific transcription factors. For example, the TTCNNNGAA core sequence of the IRF-1 GAS promoter or the mammary gland factor element (MGFe) is known to be a binding site that is highly specific for STAT5.

Oligonucleotides containing the TTCNNNGAA sequence are known to bind and form complexes with STAT5 in vitro. In fact, this forms the basis for the electrophoretic mobility shift assay (EMSA) that is performed commonly to detect activated STAT5 (and more generally to detect other STATs and other transcription factors). In this application it has been shown that the STAT5 binding sequence could compete in cells with the ability of activated STAT5 to bind to its endogenous DNA targets. Leukemic cell lines HEL/Dami and Meg-01, were found to survive and proliferate in the absence of any growth factor stimulation, express constitutively activated JAK2 and STAT5, but no other known JAK or STAT proteins or other commonly known signal transduction molecules or transcription factors could be found to be constitutively activated in this cell line.

Subsequently, it was found that inhibition of JAK2 activation with a small molecular pharmacologic agent known as AG490 or inhibition of activated STAT5 by transfection of a dominant negative STAT5 mutant inhibits HEL/Dami or Meg-01 cell proliferation. The double-stranded 20-mer oligodeoxynucleotide was designed that contains the known STAT5 binding sequence (TTCCCCGAA), and was added to the culture of HEL/Dami cells, as well as with control oligonucleotide that does not contain the STAT5 binding sequence. The specific TTCCCCGAA-containing double-stranded oligonucleotide inhibits the survival and proliferation of the HEL/Dami and Meg-01 cell lines, whereas the non-specific oligonucleotide does not inhibit specifically the survival and proliferation of these cells. Thus, specific competitive inhibition of activated STAT5 prevented the constitutively activated STAT5 from inducing proliferation of this malignant, leukemic cell line and resulted in death of the leukemic cells.

EXAMPLE 2

STAT5 Activation is Essential for Growth Factor-Independent Survival and Proliferation of HEL/Dami and Meg-01 Cell Lines:

AG490 (but not PD098059) blocked the constitutive activation of STAT5 in HEL/Dami and Meg-01 cells, but it had no effect on growth factor-induced MAPK pathway activation. Moreover, AG490 (but not PD098059) inhibited the factor-independent proliferation of HEL/Dami and Meg-01 cells in a dose-dependent manner. The constitutive is activation of JAK2 and STAT5 in HEL/Dami and Meg-01 cells, the inhibition of HEL/Dami and Meg-01 cell proliferation by AG490, and the lack of constitutive activation of the MAPK pathway in these cell lines show that the JAK2/STAT5 pathway is essential for the factor-independent growth of HEL/Dami and Meg-01 cells. By using dominant-negative (DN) STAT5 transfections the effect on factor-independent proliferation of these cell lines that express constitutively activated JAK2 and STAT5 was assessed. In order to regulate time and degree of DN-STAT5 expression, the Invitrogen ecdysone-inducible expression vector system was used. This involves double stable transfections with one vector (pVgRXR) containing the ecdysone receptor cDNA and a second vector (pIND) containing the construct of interest(e.g., DN-STAT5 cDNA) driven by an ecdysone/ muristerone/ponasterone-inducible promoter, with selection in zeocin and G418. HEL/Dami, Meg-01, and Mo7e cells stably transfected with the ecdysone receptor, and HEL/Dami cells that also contain the inducible DN-STAT5 construct in pIND were made. There was a significant muristerone dose-dependent inhibition of HEL/Dami cell proliferation only in the cells transfected with the DN-STAT5. When HEL/Dami cells were not transfected or were transfected with only pVgRXR or pIND/DN-STAT5 alone, there was no inhibition of HEL/Dami cell proliferation after addition of muristerone A. Inhibition of HEL/Dami cell survival and proliferation occurred only in cells co-transfected with pVgRXR and pIND/DN-STAT5. Ponasterone A used instead of muristerone, gave the same results.

Interference with the function of specific STAT molecules by double-stranded oligonucleotides containing the STAT nucleotide-binding domains inhibits the survival and proliferation of AML cells in vitro and in vivo in immunocompromised mice.

(a) Determine Whether Double-Stranded Oligonucleotides Containing STAT5 Nucleotide-Binding Domains Selectively Inhibit the Growth in Vitro of Primary Human AML Cells that Express Constitutively Activated STAT5

Double-stranded oligonucleotides containing the TTCNNNGAA binding site recognized by STAT5, which can competitively inhibit interaction of STAT5 with its target endogenous genes, has at therapeutic potential in those AML patients with constitutively activated STAT5 in their leukemic blast cells.

Primary AML cells are grown in 10% serum or in serum-free medium with Nutridoma HU which supports continued growth of multiple cell types. The 22–26mer double-stranded phosphorothioate-modified (to reduce degradation and increase T 1/2) oligonucleotides with 2 repeats of the STAT5 recognition sequence, TTCNNNGAA, are tested to show their ability to inhibit AML cell survival and proliferation in vitro. Control cultures contain no oligonucleotides or oligonucleotides to which STAT5 does not bind. The oligonucleotides are added into the medium in which the cells are growing and the cells are re-fed daily with approximately a 10 $\mu$M concentration of the competitive inhibitory oligonucleotide. Alternatively the oligonucleotides are introduced at (10 nM to 10 $\mu$M) in association with a cationic lipid (DOTAP or DOSPER). The same cell growth assays described above are used and demonstrates competitive inhibition of STAT5 binding to promoter elements of endogenous DNA interferes with the growth of primary human AML cells. Variations of the method can be used to maximize efficiency of AML cell growth inhibition while minimizing normal hemopoietic cell toxicity. Such methods are directly applicable to in vitro purging of leukemic cells (and other activated STAT-expressing malignant cells) from cells harvested for bone marrow and peripheral blood stem/progenitor cell transplantation.

(b) Determine Whether Modified Double-Stranded Oligonucleotides Containing STAT5 Nucleotide-Binding Domains Selectively Inhibit the Growth of AML Cells Containine Constitutively Activated STAT5 in vivo in Immunocompromised NOD/SCID Mice.

The constitutively activated STAT5-expressing cells that have been studied best in vitro (HEL/Dami and Meg-01) are used to determine the target doses of oligonucleotides that inhibit growth of human leukemic cells implanted in vivo in NOD/SCID mice. Optimal parameters are defined and used competitively inhibit STAT5 binding to endogenous DNA to inhibit proliferation and hasten apoptotic death of primary AML cells implanted in NOD/SCID mice.

Sublethally irradiated (300 cGy of TBI) NOD/SCID mice are used to support growth of human AML and blast phase CML cells in a high proportion of cases.

In dose-seeking studies, subcutaneous oligonucleotide doses of 0, 1, 5, 10, 20, and 30 $\mu$g/gm of body weight/day are administered to 5 mice per dose level, each having 1–5×10⁶ implanted HEL/Dami cells on one flank and Meg-01 cells on the other flank.

The oligonucleotides are biotinylated, and tumors are excised after the mice are sacrificed at the end of 4–6 weeks to assess oligonucleotide penetration into the leukemic cells. The first dose at which at least 3 mice have tumors that are at least 50%. smaller at 4–6 weeks than mice receiving no oligonucleotide is used in additional studies. The dose seeking studies use an estimated 5 mice/dose level×6 dose levels×2 treatments (no oligo vs. functional oligo) with 3 treatment groups—(1) sham treatment, (2) therapeutic STAT5-binding oligonucleotide, and (3) a mutated oligonucleotide that does not bind activated. The primary endpoint is the comparison of the three groups for differences in mean tumor size at 4–6 weeks, as measured by 2 perpendicular diameters of the tumor, using a one-way ANOVA. Untreated tumors average about 2×2 cm and 95% of untreated tumors are between 1.5 and 3 cm in their largest diameter at the end of 4 weeks. This study utilizes HEL/Dami leukemic cells (STAT5 constitutively activated) on one flank and TF-1a leukemic cells (no constitutively activated STATs) on the other flank. Another experiment utilizes implantation of Meg-01 leukemic cells (STAT5 constitutively activated) on one flank and U266 myeloma cells (STAT3 constitutively activated).

The growth of 12 separate samples of primary AML cells (~1–5×10⁶ cells in 5 mice each) as subcutaneous tumor implants or as circulating leukemic cells (60 mice total) is evaluated. If >50% of primary AMLs fail to grow sufficiently rapidly as tumors, tail vein injections of the primary AML cells are done to induce systemic leukemia and the survival of the mice is assessed, using Kaplan-Meier plots. Examination of morphology and CD45 expression of cells in the peripheral blood, bone marrow, and spleen is done on all such mice. Therapeutic studies are designed and have statistical considerations that are the same as those discussed above for the cell lines, except that each mouse has only one primary acute leukemia cell sample implanted on one flank, and a STAT5-positive control cell line implanted on the opposite flank.

A very high proportion of AML and blast phase CML cells grow well either as subcutaneous tumors or systemically in NOD/SCID mice (better than in nude mice). Significantly smaller tumor size and/or significantly longer survival in mice treated with the STAT5-binding oligonucleotide, as compared with sham treatment or treatment with the non-STAT5-binding mutant oligonucleotide, which indicates a selective therapeutic benefit of this treatment modality.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Agrawal, 1996. Antisense oligonucleotides: towards clinical trials, TIBTECH, 14:376.

Eckstein 1985. Nucleoside Phosphorothioates. Ann. Rev. Biochem. 54:367–402.

Iyer et al. 1990. J. Org. Chem. 55:4693–4699.

Radhakrishnan et al., 1990. The automated synthesis of sulfur-containing oligodeoxyribonucleotides using 3H-1, 2-Benzodithiol-3-0ne 1,1 Dioxide as a sulfur-transfer reagent. J. Org. Chem. 55:4693–4699.

Shaw et al., 1991. Modified deoxyoligonucleotides stable to exonuclease degradation in serum. Nucleic Acids Res. 19:747–750.

Spitzer and Eckstein 1988. Inhibition of deoxynucleases by phosphorothioate groups in oligodeoxyribonucleotides. Nucleic Acids Res. 18:11691–11704.

Woolf et al., 1990. The stability, toxicity and effectiveness of unmodified and phosphorothioate antisense oligodeoxynucleotides in Xenopus oocytes and embryos. Nucleic Acids Res. 18:1763–1769.

What is claimed is:

1. A compound for inhibiting a transcription factor in a cell, said compound comprising a double-stranded oligonucleotide, said oligonucleotide having a nucleotide sequence comprising the sequence TTCNNNGAA, wherein N represents any nucleotide, wherein said oligonucleotide comprises the sequence AGATTTCTAGGAATTCAAATC (SEQ ID NO: 1), and wherein said transcription factor binds to said oligonucleotide.

2. An agent for inhibiting a transcription factor in a cell, comprising a double-stranded oligonucleotide, said oligonucleotide having a nucleotide sequence comprising the sequence TTCNNNGAA, wherein N represents any nucleotide, wherein said oligonucleotide comprises the sequence AGATTTCTAGGAATTCAAATC (SEQ ID NO: 1) and a pharmaceutically acceptable carrier, diluent, or adjuvant.

3. The agent according to claim 2, wherein said oligonucleotide comprises multiple copies of said nucleotide sequence TTCNNNGAA.

4. The agent according to claim 2, wherein said oligonucleotide comprises two copies of said nucleotide sequence TTCNNNGAA.

5. The compound according to claim 1, wherein said tide comprises multiple copies of said nucleotide sequence TTCNNNGAA.

6. The compound according to claim 1, wherein said tide comprises two copies of said nucleotide sequence TTCNNNGAA.

7. The compound according to claim 1, wherein said oligonucleotide consists of the nucleotide sequence 5'-AGATTTCTAGGAATTCAAATC-3' (SEQ ID NO: 1).

8. The agent according to claim 2, wherein said oligonucleotide the nucleotide sequence 5'-AGATTTCTAGGAATTCAAATC-3' (SEQ ID NO: 1).

* * * * *

UNITED STATES PATENT AND TRADEMARK OFFICE
CERTIFICATE OF CORRECTION

| | | |
|---|---|---|
| PATENT NO. | : 7,002,003 B1 | |
| APPLICATION NO. | : 09/744875 | |
| DATED | : February 21, 2006 | |
| INVENTOR(S) | : Kenneth S. Zuckerman and Richard Y. Liu | |

It is certified that error appears in the above-identified patent and that said Letters Patent is hereby corrected as shown below:

Column 3,
Line 27, "(SEQ 1D NO. 2 on" should read --(SEQ ID NO. 2) on--.

Column 7,
Lines 31 and 32, "made to oligonucleotides is include" should read
--made to oligonucleotides include--.

Column 9,
Line 41, "and [P]-dATP" should read --and [$^{32}$P]-dATP--.

Column 9,
Line 51, "10' horse serum" should read --10% horse serum--.

Column 10,
Line 35, "cells 1 x 10$^6$/mL were" should read --cells (1 x 10$^6$/ml) were--.

Column 10,
Line 40, "published is protocol" should read --published protocol--.

Column 10,
Line 51-52, "by 7.5 k" should read --by 7.5%--.

Column 11,
Line 5, "(YL 1993" should read --(Yu 1993--.

Column 11,
Line 32, "and 4455 mM" should read -- 44.5 mM--.

Column 12,
Lines 11 and 12, "final is four" should read --final four--.

Column 12,
Line 14, "stimulation of [3H]" should read --stimulation of [$^3$H]-TdR--.

Column 12,
Line 66, "ISRE SEQ ID NO. 8" should read --ISRE (SEQ ID NO. 8)--.

Column 12
Line 67, "inhibition or the" should read --inhibition of the--.

UNITED STATES PATENT AND TRADEMARK OFFICE
CERTIFICATE OF CORRECTION

PATENT NO. : 7,002,003 B1
APPLICATION NO. : 09/744875
DATED : February 21, 2006
INVENTOR(S) : Kenneth S. Zuckerman and Richard Y. Liu It is certified that error appears in the above-identified patent and that said Letters Patent is hereby corrected as shown below:

Column 13,
Line 8, "$\{^{32}P\}$- labeled" should read --$[^{32}P]$-labeled--.

Column 13,
Line 13, "constitutive" should read --constitutively--.

Column 13,
Line 18, "in labeled" should read --unlabeled--.

Column 14,
Lines 52 and 53, "constitutive is activation" should read --constitutive activation--.

Column 22,
Lines 13, "wherein said tide" should read --wherein said oligonucleotide--.

Column 22,
Line 17, "wherein said tide" should read --wherein said oligonucleotide--.

Column 22,
Lines 24 and 25, "oligonucleotide the" should read --oligonucleotide consists of the--.

Signed and Sealed this

First Day of August, 2006

JON W. DUDAS
*Director of the United States Patent and Trademark Office*

SEQUENCE LISTING

<160> NUMBER OF SEQ ID NOS: 11

<210> SEQ ID NO 1
<211> LENGTH: 21
<212> TYPE: DNA
<213> ORGANISM: Artificial sequence
<220> FEATURE:
<223> OTHER INFORMATION: transcription factor binding oligonucleotide

<400> SEQUENCE: 1
agatttctag gaattcaaat c                                      21

<210> SEQ ID NO 2
<211> LENGTH: 25
<212> TYPE: DNA
<213> ORGANISM: Artificial sequence
<220> FEATURE:
<223> OTHER INFORMATION: transcription factor binding oligonucleotide

<400> SEQUENCE: 2
gcctgatttc cccgaaatga cggca                                  25

<210> SEQ ID NO 3
<211> LENGTH: 20
<212> TYPE: DNA
<213> ORGANISM: Artificial sequence
<220> FEATURE:
<223> OTHER INFORMATION: transcription factor binding oligonucleotide

<400> SEQUENCE: 3
gtatttccca gaaaaggaac                                        20

<210> SEQ ID NO 4
<211> LENGTH: 12
<212> TYPE: DNA
<213> ORGANISM: Artificial sequence
<220> FEATURE:
<223> OTHER INFORMATION: transcription factor binding oligonucleotide

<400> SEQUENCE: 4
ggggactttc cc                                                12

<210> SEQ ID NO 5
<211> LENGTH: 22
<212> TYPE: DNA

```
<213> ORGANISM: Artificial sequence
<220> FEATURE:
<223> OTHER INFORMATION: transcription factor binding oligonucleotide

<400> SEQUENCE: 5
agttgagggg actttcccag gc                                              22

<210> SEQ ID NO 6
<211> LENGTH: 9
<212> TYPE: DNA
<213> ORGANISM: Artificial sequence
<220> FEATURE:
<223> OTHER INFORMATION: transcription factor binding oligonucleotide

<400> SEQUENCE: 6 ttccccgaa                                                              9

<210> SEQ ID NO 7
<211> LENGTH: 21
<212> TYPE: DNA
<213> ORGANISM: Artificial sequence
<220> FEATURE:
<223> OTHER INFORMATION: transcription factor binding oligonucleotide

<400> SEQUENCE: 7
agcgcctccc cggccgggga g                                               21

<210> SEQ ID NO 8
<211> LENGTH: 30
<212> TYPE: DNA
<213> ORGANISM: Artificial sequence
<220> FEATURE:
<223> OTHER INFORMATION: transcription factor binding oligonucleotide

<400> SEQUENCE: 8
gatcgggaaa gggaaaccga aactgaagcc                                      30

<210> SEQ ID NO 9
<211> LENGTH: 27
<212> TYPE: DNA
<213> ORGANISM: Artificial sequence
<220> FEATURE:
<223> OTHER INFORMATION: transcription factor binding oligonucleotide

<400> SEQUENCE: 9
agcttcattt cccgtaaatc cctaagc                                         27

<210> SEQ ID NO 10
<211> LENGTH: 25
<212> TYPE: DNA
<213> ORGANISM: Artificial sequence
<220> FEATURE:
<223> OTHER INFORMATION: transcription factor binding oligonucleotide

<400> SEQUENCE: 10
catgttatgc atattcctgt aagtg                                           25

<210> SEQ ID NO 11
<211> LENGTH: 24
<212> TYPE: DNA
<213> ORGANISM: Artificial sequence
<220> FEATURE:
```

-continued

```
<223> OTHER INFORMATION: transcription factor binding oligonucleotide

<400> SEQUENCE: 11
gatccttctg ggaattccta gatc                                          24
```